Figure 1:
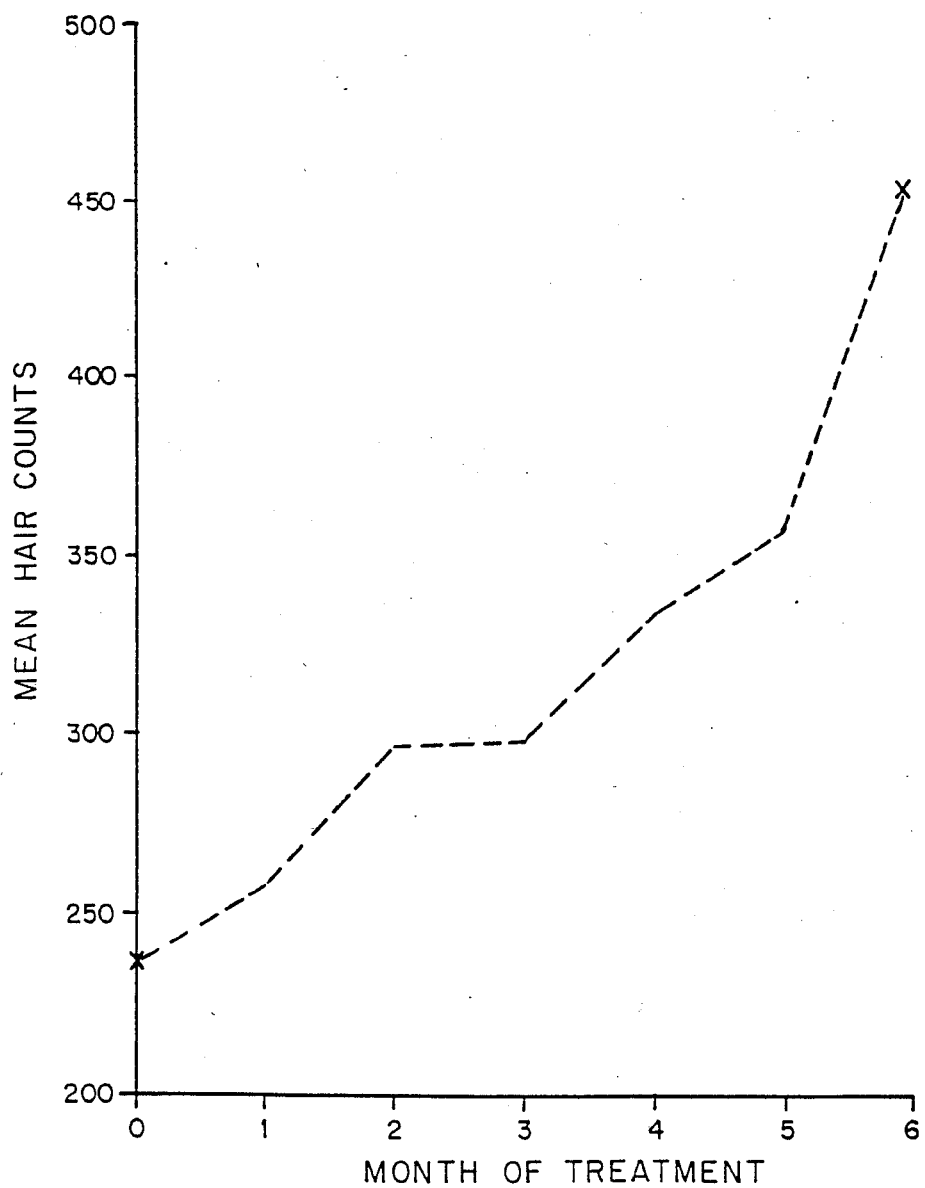
Figure 2:
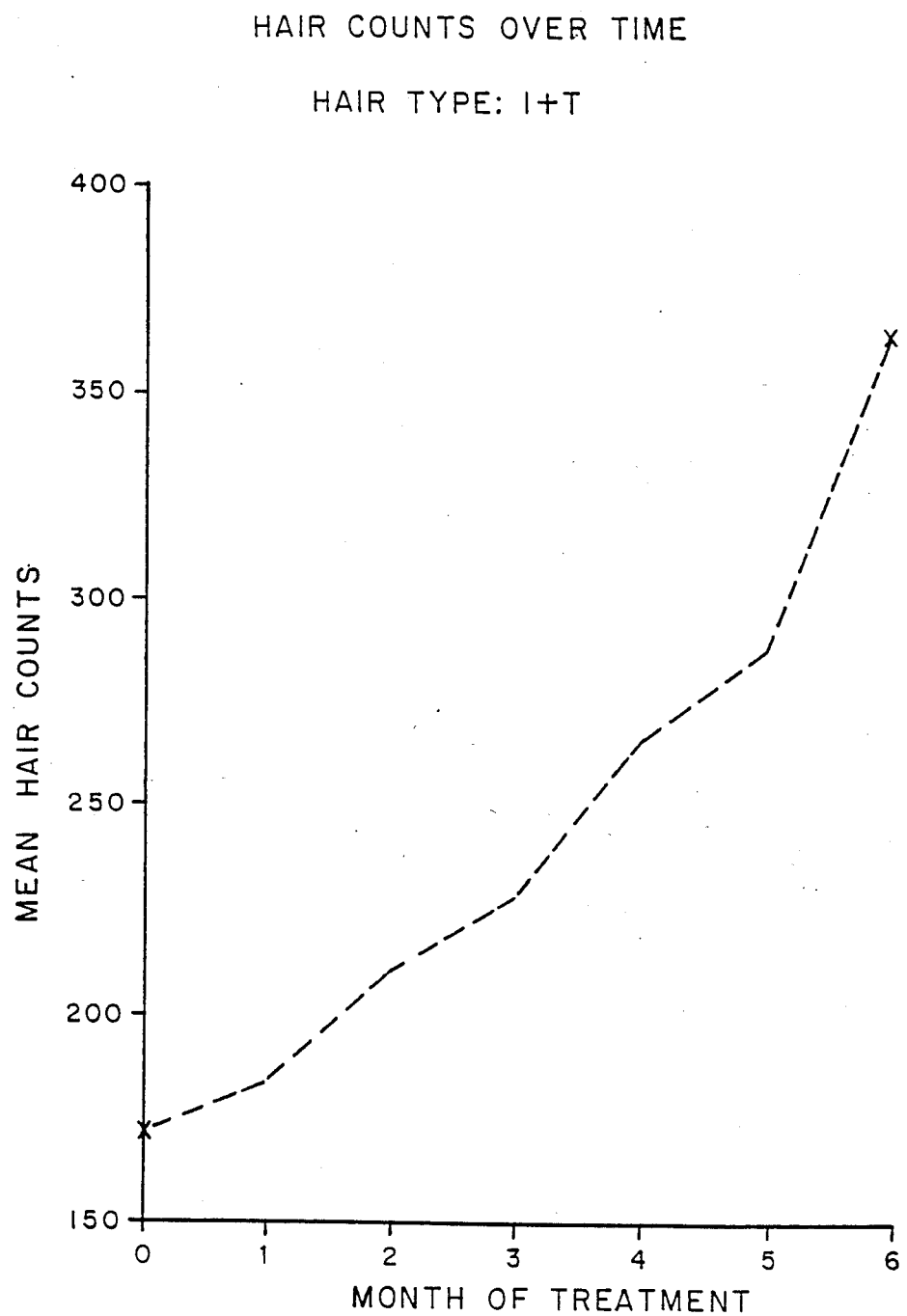
Figure 3:
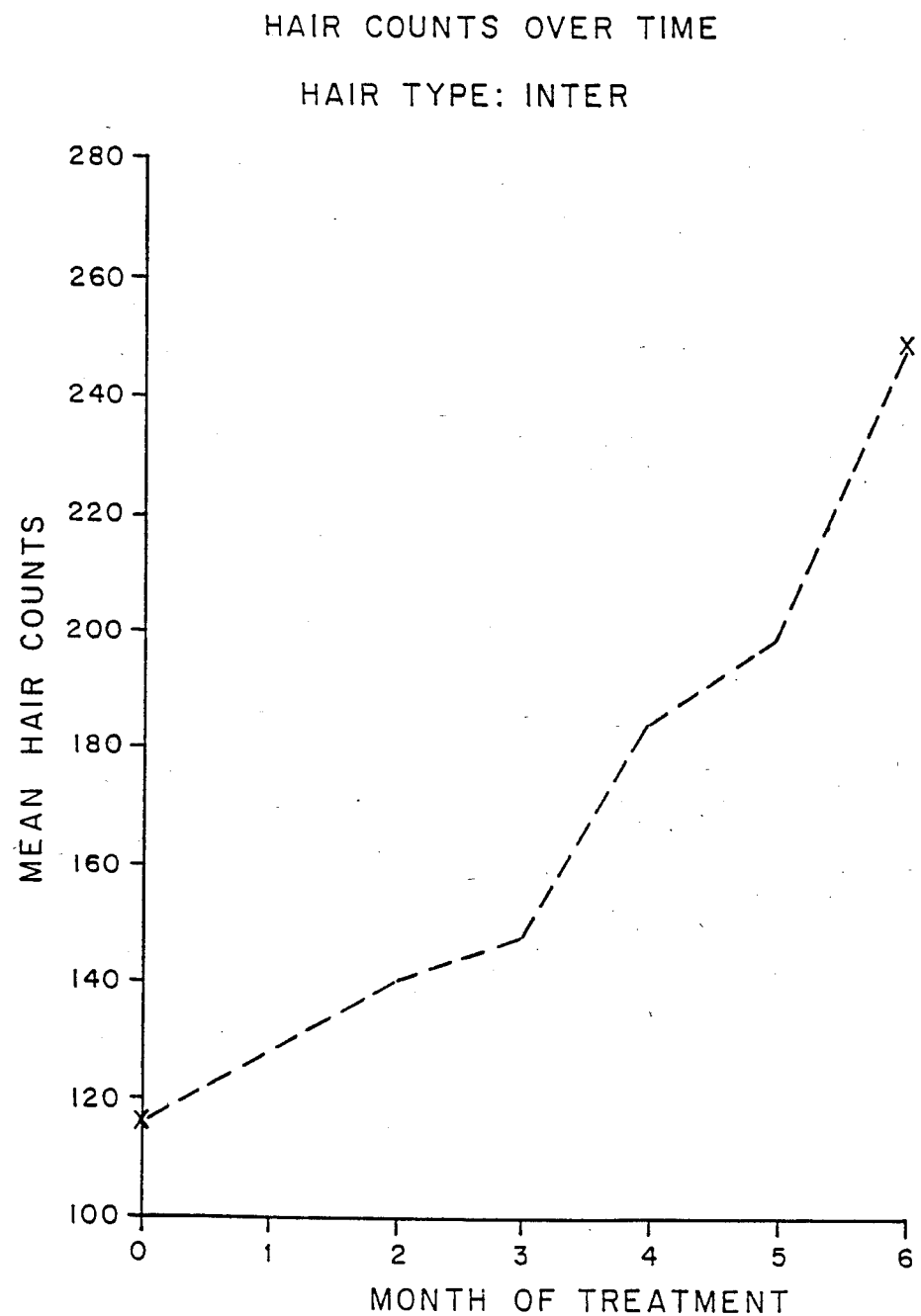
Figure 4:
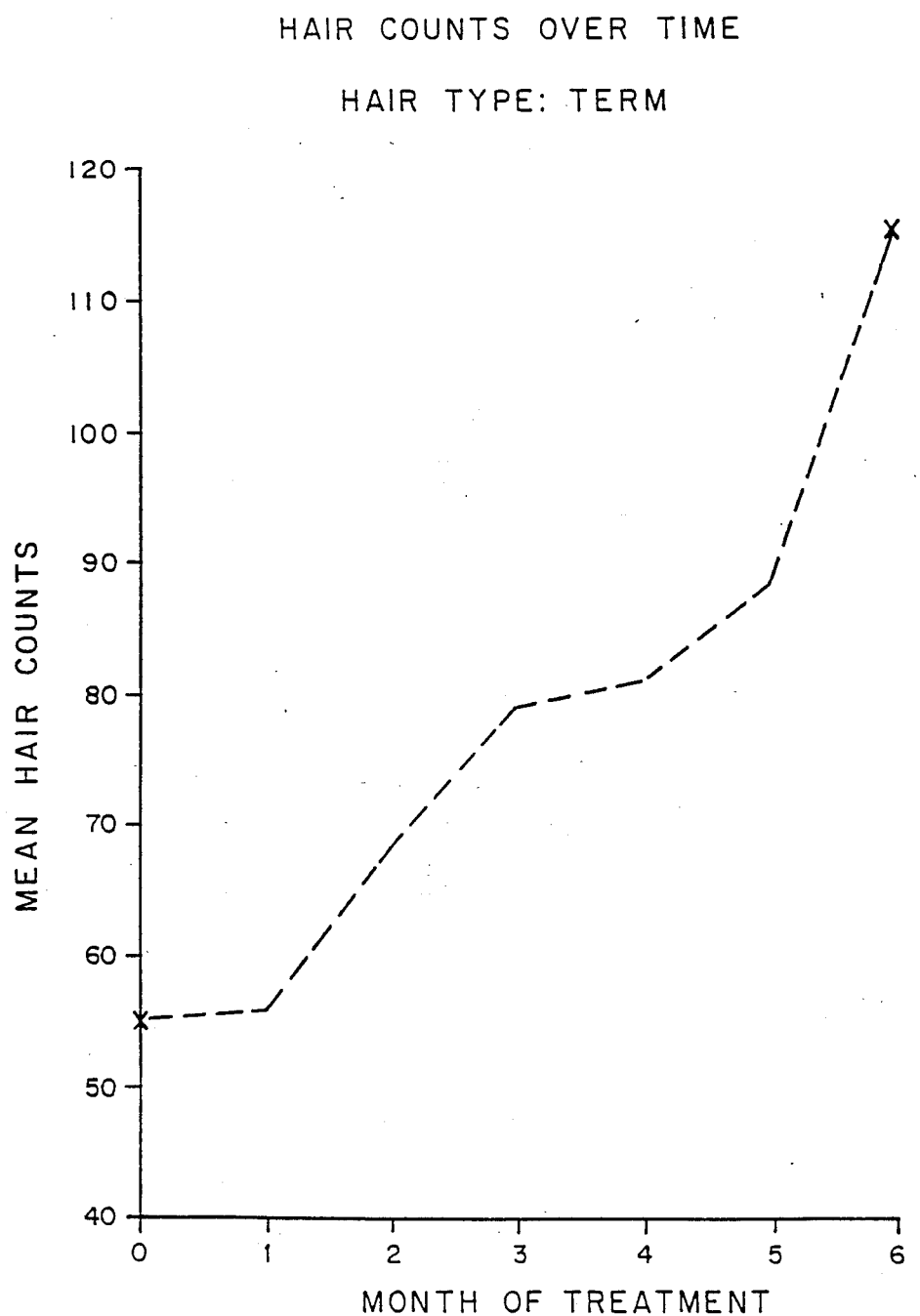
Figure 5:
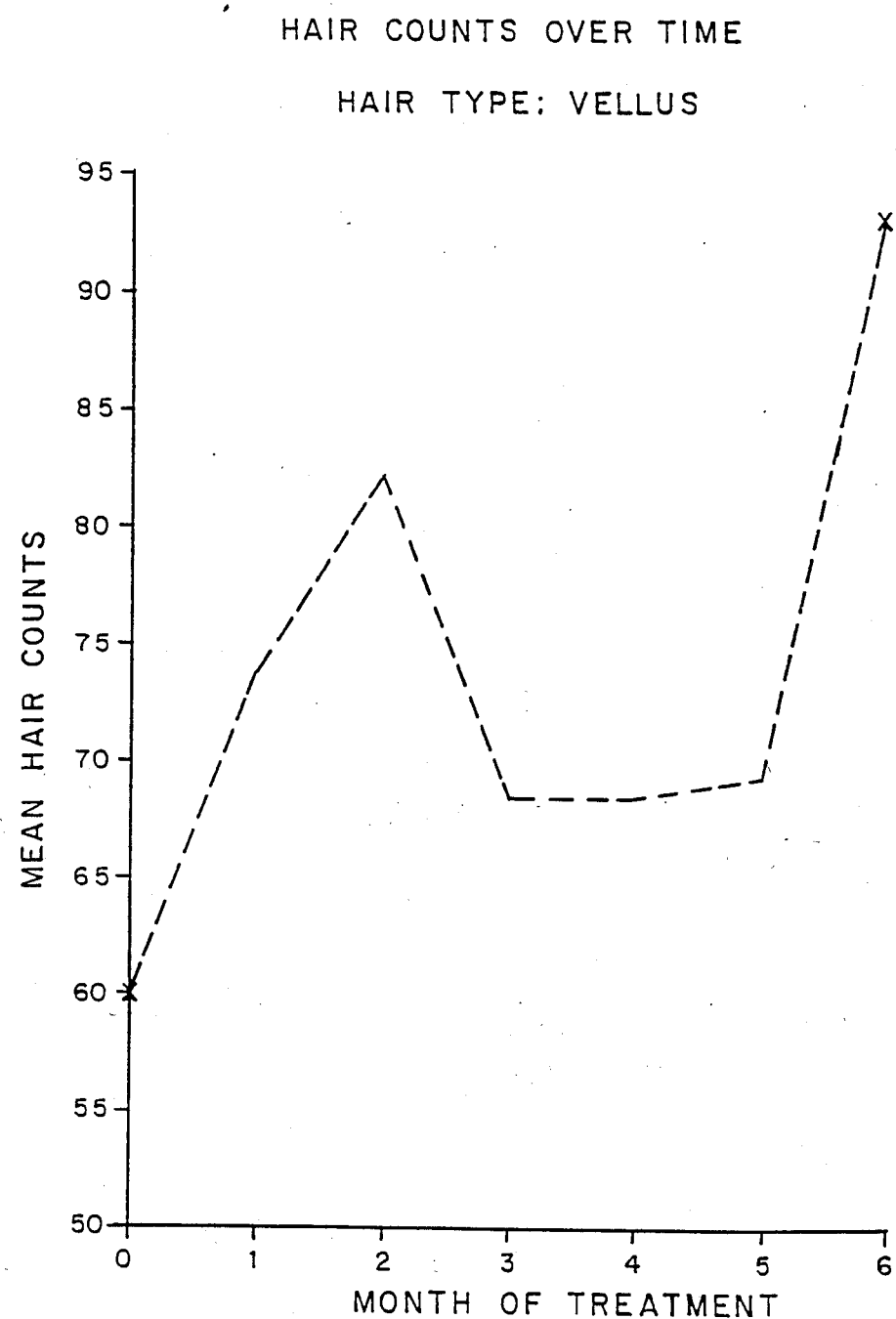

United States Patent [19]

Ritter et al.

[11] Patent Number: 4,889,845

[45] Date of Patent: Dec. 26, 1989

[54] VEHICLE FOR TOPICAL APPLICATION OF PHARMACEUTICALS

[75] Inventors: Lawrence Ritter, Suffern; James R. Lawter, Goshen, both of N.Y.

[73] Assignee: American Cyanamid Company, Stamford, Conn.

[21] Appl. No.: 145,451

[22] Filed: Jan. 19, 1988

Related U.S. Application Data

[63] Continuation of Ser. No. 870,392, Jun. 9, 1986, abandoned.

[51] Int. Cl.$^4$ ................. A61K 31/695; A61K 31/557
[52] U.S. Cl. ........................................ 514/63; 514/573
[58] Field of Search ........................... 514/63, 969, 937

[56] References Cited

U.S. PATENT DOCUMENTS 4,472,375  9/1984  Bolich, Jr. et al. ................... 424/70
4,552,755  11/1985  Randen ................................. 424/81

FOREIGN PATENT DOCUMENTS 2615654  10/1977  Fed. Rep. of Germany ........ 514/63
48-19941   6/1973  Japan ..................................... 514/63
53-142542 12/1978  Japan ..................................... 514/63
803289  10/1958  United Kingdom ................. 514/63
875780   8/1961  United Kingdom ................. 514/63

OTHER PUBLICATIONS

Current Therapy, p. 662 (1981).
Current Therapy, pp. 599–603 (1984).
Chem. Abstracts 100:12665s (1984).
Chem. Abstracts 92:152894g (1980).

Primary Examiner—Jerome D. Goldberg
Assistant Examiner—Richard Kearse
Attorney, Agent, or Firm—Robert P. Raymond

[57] ABSTRACT

A topical pharmaceutical formulation, useful as a vehicle for E-type prostaglandins is described.

7 Claims, 5 Drawing Sheets

VEHICLE FOR TOPICAL APPLICATION OF PHARMACEUTICALS

This is a continuation of application Ser. No. 870,392 filed June 9, 1986 now abandoned.

BACKGROUND OF THE INVENTION

Prostaglandins are a group of cyclic fatty acids that possess diverse and potent biologic activities affecting cellular function in every organ system. The parent compound, prostanoic acid, contains a 20 carbon chain with a cyclopentane ring.

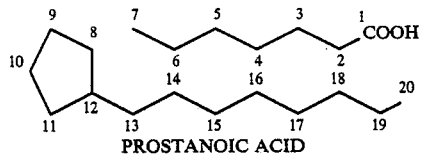

PROSTANOIC ACID

Variations in the number and position of the double bonds and hydroxyl groups determine the physiologic activities of the various prostaglandins.

Conventionally, prostaglandins are divided into types E, F, A, B, C and D based on functions in the cyclopentane ring. Numerical subscripts refer to the number of unsaturations in the side chains and, $\alpha$ or $\beta$ subscripts refer to the configuration of the substituents in the ring. The naturally occurring prostaglandins are types E, F, A and B. All naturally ocurring prostaglandins have a trans 13,14 position bond and an hydroxyl group at $C_{15}$.

The E- and F-type prostaglandins possess an additional hydroxyl at $C_{11}$. At $C_9$, E-type prostaglandins have a carbonyl function while F-type prostaglandins have an hydroxyl. In general, A- and B-type prostaglandins may be regarded as dehydration products of E-type prostaglandins; i.e., the removal of the $C_{11}$ hydroxyl and the formation of a double bond in the cyclopentane ring.

The known biologic activities of prostaglandins of the E-type include activities as hypotensive agents, brochodilators, and gastric acid secretion inhibition agents. [Bergstrom, et al., PHARMACOL., REV., 20: 1 (1968)]. However, pharmaceutical use of E-type prostaglandins has been impeded by their instability. E-type prostaglandins generally decompose slowly at room temperature and above, which decomposition is accelerated in the presence of small amounts of acid or base. Accordingly, E-type prostaglandins are unstable in pharmaceutical formulations containing water or hydroxylic compounds. Even in neutral, aqueous solution or in neat state there is a gradual decomposition of E-type prostaglandins to A- and B-type prostaglandins.

Good stability of the E-type prostaglandins has been observed in some solutions and in pure form at temperatures of $-20°$ C. or lower. However, storage at such temperatures is impractical. Some success at stabilization at room temperature has been reported when non-alcoholic compounds such as ethyl acetate and chloroform are employed as solvents for E-type prostaglandins. Such solvents, however, are unsuitable for pharmaceutical dosage applications.

More recently, good stability of E-type prostaglandins was reported with use of triethyl citrate as a solvent (U.S. Pat. No. 4,211,793) and with use of hydroxylated derivatives of fatty acids (U.S. Pat. No. 4,431,833).

THE INVENTION

It has been discovered that a formulation of: (1) polydimethylsiloxane (20 to 1,000,000 centistokes viscosity); (2) $C_{12}$–$C_{15}$ alcohols benzoate, isopropyl palmitate, isopropyl myristate, diisopropyl adipate, octyl hydroxystearate, PPG-2 myristyl ether propionate, almond oil or mixtures thereof; and (3) volatile silicones such as octamethylcyclotetrasiloxane, decamethylcyclopentasiloxane, hexamethyldisiloxane and other low molecular weight polydimethylsiloxanes and/or pharmaceutically acceptable chlorofluorocarbons. It has also been determined that such formulation provides a vehicle for stable-storage of E-type prostaglandins.

In its broadest sense the formulation of the present invention may be described as:

| Ingredient | Concentration (% by weight) |
| --- | --- |
| Polydimethylsiloxane (20 to 1,000,000 centistokes) | 1 to 50 |
| Solvent 1* | 2 to 60 |
| Solvent 2** | 100 |

*Solvent 1 may be selected from esters such as $C_{12}$-$C_{15}$ alcohols benzoate, isopropyl palmitate, isopropyl myristate, diisopropyl adipate, octyl hydroxystearate, PPG-2 myristyl ether propionate, almond oil, etc.
**Solvent 2 may be selected from volatile silicones such as octamethylcyclotetrasiloxane, decamethylcyclopentasiloxane, hexamethyldisiloxane and other low molecular weight polydimethylsiloxanes such as Dow Corning 200 Fluid 1.0 centistokes and 1.5 centistokes and pharmaceutically acceptable chlorofluorocarbons (such as the Freons).

In a specific sense, the composition according to the present invention may be described by the following formula:

| Formulation A | |
| --- | --- |
| Ingredient | Concentration (% by weight) |
| Polydimethylsiloxane (12,500 centistokes) | 15 |
| $C_{12}$–$C_{15}$ Alcohols Benzoate | 20 |
| Cyclomethicone (Octamethylcyclotetrasiloxane qs to | 100 |

The following description details the preparation of a typical formulation encompassed by this invention.

| Formulation A | | |
| --- | --- | --- |
| Ingredient | Concentration (% by Weight) | Quantity (mg/0.3 ml) |
| Polydimethylsiloxane (12,500 centistokes) | 15 | 43 |
| $C_{12}$–$C_{15}$ Alcohols Benzoate | 20 | 57.4 |
| Cyclomethicone (Octamethylcyclotetrasiloxane | qs | — |

The polydimethylsiloxane was placed in a suitable container. One half of the total quantity of cyclomethicone was added to the container and the contents were stirred until homogenous.

The $C_{12}$–$C_{15}$ alcohols benzoate was added to the polydimethylsiloxane-cyclomethicone mixture. The resulting mixture was then stirred until homogeneous.

The remaining portion of cyclomethicone was added and this final solution was stirred until homogeneous. The resulting Formulation A can then be placed into suitable containers.

Additionally, the formulation of the present invention has been determined to be useful as a pharmaceutical vehicle for topical application of E-type prostaglandin. As more fully described hereinabove, a principle problem encountered with pharmacological utilization of prostaglandins resides in their relatively unstable nature in pharmaceutical formulations. The few successful attempts at providing stable formulations have resulted in oily liquid compositions such as the triethyl citrate formulation of U.S. Pat. No. 4,211,793. Such formulation is unsatisfactory for topical application, as such results in greasy build-up on the skin. Formulation A, it has been determined, presents a suitable vehicle for topical application of E-type prostaglandins. In particular, it presents a vehicle for topical application of viprostol, methyl (±)-[11α, 5Z(5E), 13 E, 16R and 16S]-16 ethenyl-11,16-dihydroxy-9-oxoprosta-5, 13-dienloate, an E-type prostaglandin. Viprostol is active as an anti-hypertensive agent, inter alia, and can be used for such purpose with topical application. Formulation A and other formulations according to the present invention provide a non-greasy vehicle for topical application of viprostol. Additionally, viprostol may be dissolved in such vehicle without significant loss of its potency over extended periods of time at room temperature.

What is claimed is:

1. A vehicle for topical application consisting essentially of
   (a) from 1 to 50 percent by weight of a polydimethylsiloxane having a viscosity of from 20 to 1,000,000 centistokes;
   (b) from 2 to 60 percent by weight of $C_{12}$–$C_{15}$ alcohols benzoate, isopropyl palmitate, isopropyl myristate, diisopropyl adipate, octyl hydroxystearate, PPG-2 myristyl ether propionate, almond oil, or mixtures thereof; and
   (c) sufficient volatile silicones selected from the group consisting of octamethylcyclotetrasiloxane, decamethylcyclopentasiloxane and hexamethyldisiloxane, or a pharmaceutically acceptable chlorofluorocarbon to provide 100 percent by weight of said vehicle.

2. A vehicle for topical application as defined in claim 1 consisting of 15 percent by weight polydimethylsiloxane having a viscosity of about 12,500 centistokes, 20 percent by weight $C_{12}$–$C_{15}$ alcohols benzoate and sufficient cyclomethicone to provide 100 percent by weight of said vehicle.

3. A vehicle for topical application of E-type prostaglandins which consists essentially of
   (a) from 1 to 50 percent by weight of polydimethylsiloxane having a viscosity of from 20 to 1,000,000 centistokes;
   (b) from 2 to 60 percent by weight of $C_{12}$–$C_{15}$ alcohols benzoate; and
   (c) sufficient soluble silicones selected from the group consisting of octamethylcyclotetrasiloxane, decamethylcyclopentasiloxane, and hexamethyldisiloxane, or a pharmaceutically acceptable chlorofluorocarbon to provide 100 percent by weight of said vehicle.

4. A vehicle for topical application of E-type prostaglandins as defined in claim 3 which consists essentially of 15 percent by weight polydimethylsiloxane having a viscosity of about 12,500 centistokes, 20 percent by weight $C_{12}$–$C_{15}$ alochols benzoate and sufficient cyclomethicone to provide 100 percent by weight of said vehicle.

5. A vehicle for topical application which consists essentially of:
   (a) from 1 to 50 percent by weight of a polydimethylsiloxane having a viscosity of from 20 to 1,000,000 centistokes;
   (b) from 2 to 60 percent by weight of $C_{12}$–$C_{15}$ alcohols benzoate; and
   (c) sufficient cyclomethicone to provide 100 percent by weight.

6. A vehicle as defined in claim 2, which consists essentially of:
   (a) 15 percent by weight polydimethylsiloxane having a viscosity of about 12,500 centistokes;
   (b) 20 by weight of $C_{12}$–$C_{15}$ alcohols benzoate; and
   (c) sufficient cyclomethicone to provide 100 percent by weight.

7. A formulation which consists of:
   (a) from 1 to 50 percent by weight of a polydimethylsiloxane having a viscosity of from 20 to 1,000,000 centistokes;
   (b) from 2 to 60 percent by weight of $C_{12}$–$C_{15}$ alcohols benzoate; and
   (c) sufficient cyclomethicone to provide 100 percent by weight.

* * * * *